United States Patent [19]

Croze

[11] Patent Number: 5,151,504

[45] Date of Patent: Sep. 29, 1992

[54] METHOD FOR PURIFICATION OF MONOCLONAL ANTIBODIES

[75] Inventor: Edward M. Croze, San Ramon, Calif.

[73] Assignee: E. R. Squibb & Sons, Inc., Princeton, N.J.

[21] Appl. No.: 500,340

[22] Filed: Mar. 26, 1990

Related U.S. Application Data

[63] Continuation-in-part of Ser. No. 438,548, Nov. 17, 1989.

[51] Int. Cl.$^5$ ............................. C07K 3/18; C07K 3/28
[52] U.S. Cl. ................................ 530/413; 530/387.1; 530/389.1; 530/412
[58] Field of Search ............... 530/412, 413, 382, 389, 530/391

[56] References Cited

U.S. PATENT DOCUMENTS

| | | | |
|---|---|---|---|
| 4,415,665 | 11/1983 | Mosbach et al. | 435/179 |
| 4,704,366 | 11/1987 | Juarez-Salinas et al. | 436/501 |
| 4,801,687 | 1/1989 | Ngo | 530/387 |
| 5,089,605 | 2/1992 | Profer et al. | 530/402 |

FOREIGN PATENT DOCUMENTS

| | | |
|---|---|---|
| 0282308 | 9/1988 | European Pat. Off. |
| 0284368 | 9/1988 | European Pat. Off. |
| 0310719 | 4/1989 | European Pat. Off. |
| WO87/05025 | 8/1987 | PCT Int'l Appl. |
| WO88/10306 | 12/1988 | PCT Int'l Appl. |
| 1563355 | 3/1980 | United Kingdom |

OTHER PUBLICATIONS

FASEB Journal, vol. 3, No. 4, p. A1379 (1989) "Antibody Purification and Detection with Recombinant Protein G".

Jungbauer, A. et al., J. Chromatogr. 476, 257–268 (1989) "Comparison of Protein A, Protein G and Copolymerized Hydroxyapatite for the Purification of Human Monoclonal Antibodies".

Falkenberg, C. et al., Biomed. Chromatogr. 2, 221–225 (1987), "Purification of Streptococcal Protein G Expressed by *Escherichia coli* by High Performance Liquid Affinity Chromatography Using Immobilized Immunoglobulin G and Albumin".

Ohlson, S. et al., J. Immunol. Methods, 114, 175–180 (1988) "A Novel Approach to Monoclonal Antibody Separation using High Performance Liquid Affinity Chromatography (HPLAC) with SelecitSpher-10 Protein G".

Delacroix, D. et al., Molecular Immunology 16, 837–840 (1979) "Simple Purification of Goat IgG1 and IgG2 Subclasses by Chromatography on Protein A-Sepharose at Various pH".

Akerstrom, B. et al., J. Immunol. 135, 2589–2592 (1985) "Protein G: A Powerful Tool for Binding and Detection of Monoclonal and Polyclonal Antibodies".

Zymed Laboratories, Inc., (1989–1990) pp. 75–77 "Protein G Reagents" and pp. 89–90 Antibody Purification.

Primary Examiner—Merrell C. Cashion, Jr.
Assistant Examiner—Andrew G. Rozycki
Attorney, Agent, or Firm—James M. Bogden

[57] ABSTRACT

An improved method for the purification of monoclonal antibodies using Protein G, whereby the monoclonal antibodies are eluted from the Protein G at alkaline pH.

16 Claims, 1 Drawing Sheet

METHOD FOR PURIFICATION OF MONOCLONAL ANTIBODIES

BACKGROUND OF THE INVENTION

The fusion of mouse myeloma cells to spleen cells from immunized mice by Kohler and Milstein in 1975 [Nature 256, 495-497 (1975)] demonstrated for the first time that it was possible to obtain continuous cell lines making homogeneous (so-called "monoclonal") antibodies. Since this seminal work, the need has existed for methods for the purification of monoclonal antibodies. Various cell surface proteins expressed by different strains of bacteria have been employed for this purpose. For example, Protein A, a protein isolated from *Staphylococcus aureus* which binds to the Fc region of immunoglobulins, and Protein G, an immunoglobulin binding, bacterial cell wall protein isolated from group G streptococcus bacteria, have been employed in the purification of both monoclonal and polyclonal antibodies. Protein G has been shown to bind to various animal and human antibodies, including bovine, chicken, goat, mouse, rabbit and rat polyclonal IgG, some mouse monoclonal antibodies, and human IgG1, IgG2, IgG3 and IgG4, in addition to albumin from various sources.

Despite this knowledge, there is a need for improved methods for the purification of monoclonal antibodies utilizing Protein G.

SUMMARY OF THE INVENTION

The present invention concerns improved methods for the purification of monoclonal antibodies.

In particular, the present invention comprises improved methods for the purification of monoclonal antibodies using Protein G bound to a substrate, wherein the improvement comprises eluting the monoclonal antibodies from the particle bound Protein G using a buffer solution of alkaline pH. The methods of the present invention are particularly suited for the purification of monoclonal antibodies of the subclass $IgG_1$.

DETAILED DESCRIPTION OF THE INVENTION

Figure 1:
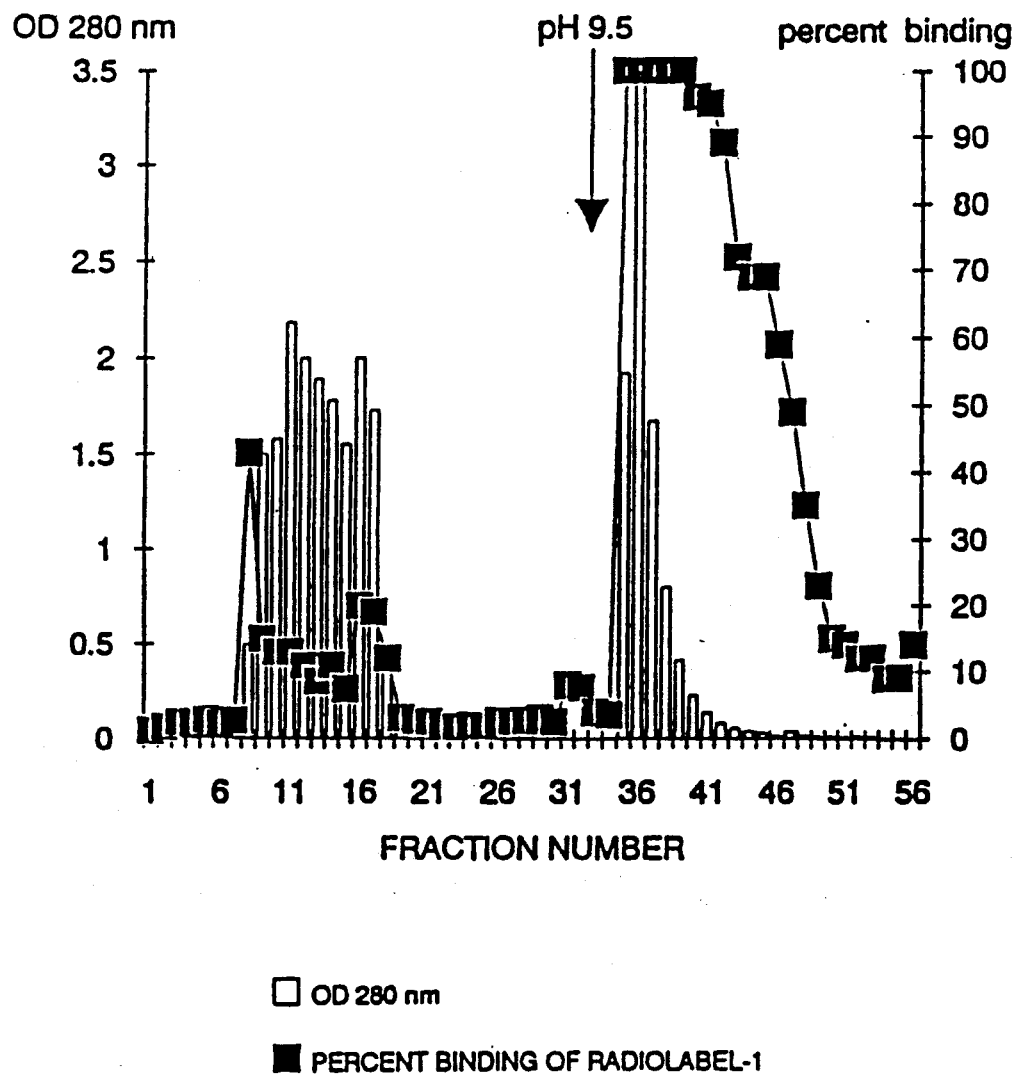
FIG. 1 shows the purification of an $IgG_1$ monoclonal antibody, MCTX1, by Protein G affinity chromatography.

As noted above, the present invention concerns improved methods for the purification of monoclonal antibodies.

In particular, the present invention concerns an improved method for the purification of monoclonal antibodies using Protein G bound to a substrate, wherein the improvement comprises eluting the monoclonal antibodies from the substrate bound Protein G using a buffer solution of alkaline pH.

The present invention further concerns a method for the purification of monoclonal antibodies comprising:

(a) applying a preparation containing monoclonal antibodies to an absorbant which removes contaminants from the preparation;

(b) eluting the monoclonal antibodies from the absorbant;

(c) absorbing the monoclonal antibodies onto Protein G bound to a substrate (d) eluting the monoclonal antibodies from the substrate bound Protein G using a buffer solution of alkaline pH; and (e) recovering the purified monoclonal antibodies.

Various monoclonal antibodies may be purified using the methods of the present invention. Preferred are monoclonal antibodies of the IgG class produced by hybridomas formed by the fusion of mouse spleen cells and mouse myeloma cells. Particularly preferred are monoclonal antibodies of the $IgG_1$ subclass produced by murine hybridomas.

The methods of the present invention may be used to purify monoclonal antibodies present in various antibody containing preparations. For example, monoclonal antibodies present in the ascites fluid of syngeneic mammals (e.g., mice) which have been produced by growing hybridoma cells in the intraperitoneal cavity of the syngeneic mammals in vivo, or monoclonal antibodies present in cell culture supernatants which have been produced by culturing hybridoma cells (e.g., murine hybridomas) in vitro may be so purified.

The present invention involves the absorption of monoclonal antibodies onto Protein G bound to a substrate. Various forms of Protein G may be used, the only requirement being that the Protein G molecule possess the ability to bind the immunoglobulin which is to be purified. For example, Protein G isolated from natural sources, Protein G produced by recombinant DNA techniques, modified forms of Protein G, or fragments of these materials which retain immunoglobulin binding ability may be employed. Preferably, the Protein G is a recombinantly produced, modified form of Protein G sold under the trademark REC-PROTEIN G by Zymed Laboratories (South San Francisco, Calif.).

Various substrates may be used to bind the Protein G. For example, beaded agarose particles such as Sepharose 4B, which may be obtained from Pharmacia (Piscataway, N.J.) may be employed. A recombinantly produced, modified form of Protein G bound to Sepharose 4B and sold under the trademark REC-PROTEIN G SEPHAROSE may be obtained from Zymed Laboratories.

Various procedures known in the art may be used to bind Protein G to a substrate. For example, if beaded agarose particles such as Sepharose 4B are employed as the substrate, the particles may be activated with cyanogen bromide, and the Protein G coupled to the activated particles.

The substrate bound Protein G may be utilized in various ways. For example, the substrate bound Protein G may be packed into a column, and a column procedure employed. Alternatively, a batch procedure may be employed.

The monoclonal antibodies may be absorbed onto the substrate bound Protein G using various procedures. For example, if a column procedure is employed, the monoclonal antibodies may be absorbed to the column using a buffer solution prepared with an appropriate buffer, for example, phosphate, MOPS and HEPES. The pH of the buffer solution may vary from about 5.0 to about 6.0, while the ionic strength may vary from about 0.05 M to about 0.1 M. Preferably, the buffer solution is 0.1 M sodium phosphate, pH 5.5.

The monoclonal antibodies may be eluted from the substrate bound Protein G using various procedures. For example, if a column procedure is employed, the monoclonal antibodies may be recovered by eluting the monoclonal antibodies from the column using a buffer solution prepared with an appropriate alkaline buffer. Appropriate alkaline buffers include, for example, glycine and sodium carbonate. The pH of the buffer solution may vary from about 9.5 to about 10.0, while the ionic strength may vary from about 0.1 M to about 0.5 M. Preferably, the buffer solution is 0.1 M glycine, pH 9.5.

Optionally, either before or after the Protein G purification step, absorbants may be used to remove contaminants present in the antibody containing preparation. For example, ion exchange resins such as DEAE Sepharose (Pharmacia), or cross-linked agarose gels containing contaminant binding moieties may be employed. Particularly preferred is CMAffi-Gel Blue obtained from Bio-Rad Laboratories (Richmond, Calif.), which is a beaded cross-linked agarose gel containing a cibacron blue F3GA dye, and which has ligand specificity for albumin and serum proteases.

The absorbants used to remove contaminants present in the antibody containing preparation may be utilized in various ways. For example, the absorbant may be packed into a column, and a column procedure employed. Alternatively, a batch procedure may be employed.

The monoclonal antibodies may be applied to and eluted from the absorbant used to remove contaminants from the antibody containing preparation using various procedures. For example, if a column procedure is employed, the monoclonal antibodies may be applied to and eluted from the column using appropriate buffer solutions. The identity of the buffer, and the pH an dionic strength of the buffer solution, will vary depending on the nature of the absorbant. Appropriate buffers include, for example, phosphate and TRIS buffers. The pH of the buffer solution will typically range from about 6.5 to about 7.5, while the ionic strength will typically range from about 0.15 M to about 0.2 M. Preferably, the same application and elution buffer, for example, phosphate buffered saline (PBS) (55 mM sodium phosphate, pH 7.3 containing 150 mM NaCl), is employed.

The elution of monoclonal antibodies from either the absorbant which removes contaminants from the preparation containing monoclonal antibodies, or from the substrate bound Protein G may be monitored by various methods well-known in the art. For example, if column procedures are employed, fractions may be collected from the columns, and the presence of protein determined by measuring the absorption of the fractions at a wavelength of 280 nm. If monoclonal antibodies of known specificity are being purified, the presence of monoclonal antibodies in fractions collected from the columns may be measured by immunoassay techniques, for example, radioimmunoassay (RIA) or enzyme immunoassay (EIA).

The methods of the present invention may be performed at any convenient temperature which does not substantially degrade the monoclonal antibodies being purified, or detrimentally effect the Protein G bound to a substrate, or the contamination removing absorbant. Temperatures ranging from about 4° C. to about 25° C. may be employed. Preferably, the temperature employed is room temperature.

The monoclonal antibodies which are eluted from the Protein G column may be recovered using various methods known in the art. For example, the column fractions may be pooled, concentrated and dialyzed to remove excess salts. For short term storage, the resulting antibody solution may then be refrigerated at 4° C. in phosphate buffered 0.05% sodium azide. For long term storage, the resulting antibody solution may be frozen and stored at −20° C. or lyophilized to dryness, and the resulting antibody preparation stored at −20 C.

Although the present invention is particularly adapted to the purification of monoclonal antibodies, it may also be used for the purification of other antibodies, for example, polyclonal antibodies, or fragments of monoclonal or polyclonal antibodies.

The following example is further illustrative of the present invention. This example is not intended to limit the scope of the present invention, and provides further understanding of the invention.

EXAMPLE

Purification of Monoclonal Antibodies

Hybridomas secreting a murine monoclonal antibody of class IgG, subclass $IgG_1$, designated MCTX1, were inoculated into pristine-treated BALB/c mice to produce ascites fluid, which was used as starting material for the isolation of MCTX1. Ascites fluid was collected from four different mice and the amount of MCTX1 present was titrated by RIA. All four mice produced ascites fluid containing MCX1 at concentrations significantly greater than that found in antibody containing media. Ascites fluid from all four animals was pooled and used as starting material to isolate MCTX1.

Ascites fluid containing monoclonal antibody MCTX1 was diluted 1:1 with 2×PBS and applied to a 1.5×100 cm CM Affi-Gel Blue Column pre-equilibrated with PBS. Fractions (2.0 ml) were collected at a flow rate of 0.5 ml/min and protein eluting from the column was monitored by determining the absorbance at 280 nm for each sample. The elution of MCTX1 from the column was monitored by RIA. CM Affi-Gel Blue chromatography removes albumin, complement proteins, and serum proteases from the sample, thereby enriching the fraction for MCTX1. Serum proteins such as these bind to the column whereas immunoglobulins do not. MCTX1 therefore elutes after the void volume. Protein was detected beginning with fraction 10 and ending at fraction 20. Both protein and MCTXI began eluting from the column at the same time. However, MCTX1 continued to emerge from the column during a time when protein could not be detected by UV absorption spectroscopy.

CM Affi-Gel Blue Column fractions 14 to 24 containing MCTXI were collected, pooled, dialyzed overnight at 4° C. against 55 mM sodium phosphate, pH 7.0 and concentrated using Aquacide II (Calbiochem). The resulting sample was adjusted to pH 5.5 with 0.1 M glycine, pH 3.5 and applied to a 1.5 cm×8.0 cm recombinant Protein G-Sepharose 4B column (Zymed Laboratories) pre-equilibrated with 0.1 M sodium phosphate, pH 5.5. The column was then washed with 50 ml of 0.1 M sodium phosphate, pH 5.5 at a flow rate of 0.5 ml/min. Bound MCTX1 was eluted from the column by washing the column with 15 ml of 0.1 M glycine, pH 9.5 at a flow rate of 0.5 ml/min. Fractions (1.0 ml) were collected in test tubes containing 100 μl of 1.0 M. Tris-buffer, pH 7.0 which neutralized the resultant samples. The protein concentrate was calculated using an extinction coefficient for immunoglobulin of $\epsilon = 1.41$ $cm^2/mg$. MCTX1 was detected by specific RIA and expressed as percent binding of radioligand.

The recombinant form of Protein G binds to the Fc region of IgG immunoglobulins at low pH (pH 5.5). Applicant has found that this binding can be reversed at high pH (pH 9.5 to 10), thereby providing a convenient method for affinity purifying immunoglobulins. The bulk of the protein eluted from the Protein G affinity column immediately after the void volume (FIG. 1). MCTXl, however, was eluted by washing the column with 0.1 M glycine, pH 9.5. The small amount of MCTXI co-eluting with the first protein peak may reflect the presence of a population of MCTXl having an altered Fc region or a limitation in the binding capacity of the Protein G affinity column. Only fractions eluting from the affinity column after washing with alkaline buffer were collected. Fractions containing this form of MCTXl were pooled, concentrated and dialyzed against PBS.

DETAILED DESCRIPTION OF THE DRAWING

FIG. 1: Material from ascites fluid enriched for MCTXl was subjected to Protein G affinity chromatography. Affinity purified MCTXI eluted from the column after washing the column with alkaline buffer, pH 9.5.

What is claimed is:

1. An improved method for the purification of antibodies of the Class IgG or antibody fragments of the class IgG comprising:

(a) applying a preparation containing antibodies of the Class IgG or antibody fragments of the class IgG to an absorbant which removes contaminants from the preparation;

(b) eluting the antibodies of the Class IgG or antibody fragments of the class IgG from the absorbant;

(c) absorbing the antibodies of the Class IgG or antibody fragments of the class IgG onto Protein G bound to a substrate;

(d) eluting the antibodies of the Class IgG or antibody fragments of the class IgG from the substrate bound Protein G with a solution of alkaline pH; and (e) recovering the purified antibodies of the Class IgG or antibody fragments of the class IgG, wherein the purified antibodies fragments of the class IgG, wherein the purified antibodies or antibody fragments retain the ability to bind antigen.

2. The method according to claim 1 wherein the absorbant in step (a) is CM Affi-Gel Blue.

3. The method according to claim 2 wherein the CM Affi-Gel Blue is contained in a column.

4. In a method for the purification of antibodies of the Class IgG or antibody fragments of the class IgG using Protein G bound to a substrate, the improvement comprising eluting the antibodies of the Class IgG or antibody fragments of the class IgG from the substrate bound Protein G with a solution of alkaline pH, wherein the purified antibodies or antibody fragments retain the ability to bind antigen.

5. The method according to claims 1 or 4 wherein the pH of the eluant used to elute the antibodies of the Class IgG or antibody fragments of the class IgG from the substrate bound Protein G ranges from about 9.5 to about 10.0.

6. The method according to claim 5 wherein the pH of the eluant used to elute the antibodies of the Class IgG or antibody fragments of the class IgG from the substrate bound Protein G is about 9.5.

7. The method according to claim 5, wherein the eluent comprises a glycine solution of a concentration ranging from about 0.1 M to about 0.5 M.

8. The method according to claim 7, wherein the glycine concentration is about 0.1 M.

9. The method according to claims 1 or 4 wherein the antibodies of the Class IgG or antibody fragments of the class IgG are of the subclass IgGl.

10. The method according to claims 1 or 4 wherein the substrate is a beaded agarose particle.

11. The method according to claims 1 or 4 wherein the Protein G is recombinant Protein G.

12. The method according to claims 1 or 4 wherein the substrate bound Protein G is contained in a column.

13. The method according to claims 1 or 4 wherein the antibodies are monoclonal antibodies.

14. The method according to claim 13 wherein the pH of the eluant used to elute the monoclonal antibodies from the substrate bound Protein G ranges from about 9.5 to about 10.0.

15. The method according to claim 13 wherein the preparation containing monoclonal antibodies is ascite fluid.

16. The method according to claim 13 wherein the preparation containing monoclonal antibodies is a cell culture supernatant.

* * * * *